(12) United States Patent
Dromard et al.

(10) Patent No.: US 10,874,478 B2
(45) Date of Patent: Dec. 29, 2020

(54) TREATMENT MACHINE OF A MEDICAL APPARATUS

(71) Applicant: Ecolab USA Inc., Saint Paul, MN (US)

(72) Inventors: Tanguy Dromard, Marseilles (FR); Eric Pendaries, La Ciotat (FR); Sebastien Ruiz, Rognac (FR)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/584,407

(22) Filed: Sep. 26, 2019

(65) Prior Publication Data

US 2020/0015932 A1 Jan. 16, 2020

Related U.S. Application Data

(62) Division of application No. 14/123,542, filed as application No. PCT/EP2012/002383 on Jun. 5, 2012, now Pat. No. 10,463,448.

(30) Foreign Application Priority Data

Jun. 6, 2011 (FR) ..................................... 11 01734

(51) Int. Cl.
  *A61B 90/70* (2016.01)
  *B08B 9/023* (2006.01)
  *B05B 1/20* (2006.01)

(52) U.S. Cl.
  CPC .............. *A61B 90/70* (2016.02); *B08B 9/023* (2013.01); *A61B 2090/701* (2016.02); *B05B 1/20* (2013.01)

(58) Field of Classification Search
  None
  See application file for complete search history.

(56) References Cited

U.S. PATENT DOCUMENTS

| | | | |
|---|---|---|---|
| 4,278,101 | A | 7/1981 | Tanaka et al. |
| 4,489,741 | A | 12/1984 | Ogasawara |

(Continued)

FOREIGN PATENT DOCUMENTS

| | | |
|---|---|---|
| DE | 10053177 A1 | 5/2001 |
| EP | 1839565 A2 | 10/2007 |

(Continued)

OTHER PUBLICATIONS

International Patent Application No. PCT/EP2012/002383, International Search Report and Written Opinion dated Jul. 25, 2012, 16 pages (including 7 pages English Translation).

*Primary Examiner* — Mikhail Kornakov
*Assistant Examiner* — Pradhuman Parihar
(74) *Attorney, Agent, or Firm* — Fredrikson & Byron, P.A.

(57) ABSTRACT

A treatment machine for a medical apparatus having inner portions and outer portions, contains a hollow vessel for receiving the medical apparatus, a first treatment system for treating the inner portions and a second treatment system for treating the outer portions. The first treatment system includes: an element for connecting at least one end piece of the medical apparatus to circulate treatment liquid in its inner portion, and the second treatment system includes: at least one spray nozzle for receiving and projecting vigorously at least one pressurized treatment liquid into the volume of the vessel to treat the outer portions of the medical apparatus and the inner surfaces of the vessel by spraying while creating a mechanical and chemical effect, and at least one element for filling the vessel with treatment liquid, to treat the outer portions of the medical apparatus and the inner surfaces of the vessel by immersing.

11 Claims, 1 Drawing Sheet

(56) References Cited

U.S. PATENT DOCUMENTS

| | | |
|---|---|---|
| 4,690,159 A | 9/1987 | Vadakin et al. |
| 5,765,581 A | 6/1998 | Badger et al. |
| 6,494,222 B1 | 12/2002 | Mitsumori et al. |
| 2002/0182105 A1* | 12/2002 | Nakanishi .......... A61B 1/00059 |
| | | 422/28 |
| 2003/0190256 A1* | 10/2003 | Halstead ................ A61B 1/123 |
| | | 422/28 |
| 2004/0134520 A1 | 7/2004 | Weber |
| 2007/0107755 A1* | 5/2007 | Noguchi .................... A61L 2/18 |
| | | 134/94.1 |
| 2007/0185385 A1* | 8/2007 | Noguchi ................ A61B 1/123 |
| | | 600/132 |
| 2009/0205687 A1 | 8/2009 | Onishi et al. |
| 2009/0241987 A1 | 10/2009 | Serizawa et al. |
| 2011/0197632 A1 | 8/2011 | Lu et al. |

FOREIGN PATENT DOCUMENTS

| | | |
|---|---|---|
| EP | 2105147 A1 | 9/2009 |
| JP | 2000166869 A | 6/2000 |

\* cited by examiner

TREATMENT MACHINE OF A MEDICAL APPARATUS

This patent application is a divisional of U.S. patent application Ser. No. 14/123,542, filed Jan. 8, 2014, which is a US National Phase Patent Application of International Patent Application No. PCT/EP2012/002383, filed Jun. 5, 2012, which claims priority to FR Patent Application No. 11/01734, filed on Jun. 6, 2011. The content of each of these applications is incorporated herein by reference.

FIELD OF THE INVENTION

Disclosed in the present invention is a treatment machine of a medical apparatus, such as a flexible endoscope.

BACKGROUND

In the field of treatment of medical apparatus, the use of treatment machines and of automation have provided with respect to manual treatment, better performances with increased repeatability, reduced treatment time, while reducing potentially dangerous exposure of the staff to cleaning products.

A processing machine performs a succession of cleaning and disinfection operations in a set order. It must meet the regulatory constraints as specified in the standards ISO 15883-1 and ISO 15883-4.

The treatment machines known today operate, for the inner portions as well as for the outer portions of the medical apparatus, by immersing said medical apparatus into the cleaning/disinfection products, whereas treating the inner portions of the medical apparatus consists in passing said cleaning/disinfection products into the channels of the medical apparatus. As said treatment products cannot be re-used from one medical apparatus to the other, immersing causes excessive consumption of the treatment products. This leads to high purchasing costs of the products, to which post-treatment costs can be added, since said products are potentially polluting.

SUMMARY OF THE INVENTION

The present invention remedies these various shortcomings.

A first object of the invention is directed to a processing machine for a medical apparatus (2) comprising inner portions and outer portions, such as a flexible endoscope, whereas said machine contains a hollow vessel (3) capable of receiving said medical apparatus (2), a first treatment system (4) capable of treating the inner portions of the medical apparatus (2) and a second treatment system capable of treating the outer portions of the medical apparatus (2), wherein:

said first treatment system comprises a means for connecting at least one end piece of the medical apparatus so as to enable treatment liquid to circulate in its inner portion, preferably a means for connecting the different end pieces of the medical apparatus (2) so as to establish the circulation of treatment liquid in a leak-proof manner and in that said second treatment system comprises:
at least one spray nozzle (6) capable of receiving at least one pressurised treatment liquid and of projecting vigorously said treatment liquid into the volume of the vessel (3), so as to perform a treatment of the outer portions of the medical apparatus (2) and of the inner surfaces of the vessel (3) by spraying while creating a mechanical effect and a chemical effect,
still at least one means for filling the vessel (3) capable of filling, at least partially, said vessel (3) with at least one treatment liquid, so as to perform a treatment of the outer portions of the medical apparatus (2) and the inner surfaces of the vessel (3) by immersing, at least partially.

A second object of the invention is directed to a method for treating a medical apparatus (2) comprising inner portions and outer portions, such as a flexible endoscope, by means of a machine as defined in the claim 1, including the following steps:
spraying the outer portions of the medical apparatus (2) and the inner surfaces of the vessel (3) with at least one treatment liquid by means of at least one spray nozzle (6),
immersing, at least partially, the outer portions of the medical apparatus (2) and the inner surfaces of the vessel (3) into at least one treatment liquid by filling, at least partially, the vessel (3) by means of said filling means, whereas said immersing step is performed prior, concomitantly or posterior to the spray step,
treating the inner portions of the medical apparatus using the first treatment system (4) comprising a means for connecting at least one end piece of the medical apparatus so as to enable treatment liquid to circulate in its inner portion, preferably a means for connecting the different end pieces of the medical apparatus (2) so as to establish a circulation of treatment liquid in a leak-proof manner, whereas said treatment step is performed prior, concomitantly or posterior to the spray and/or immersing steps.

DETAILED DESCRIPTION

Figure 1:
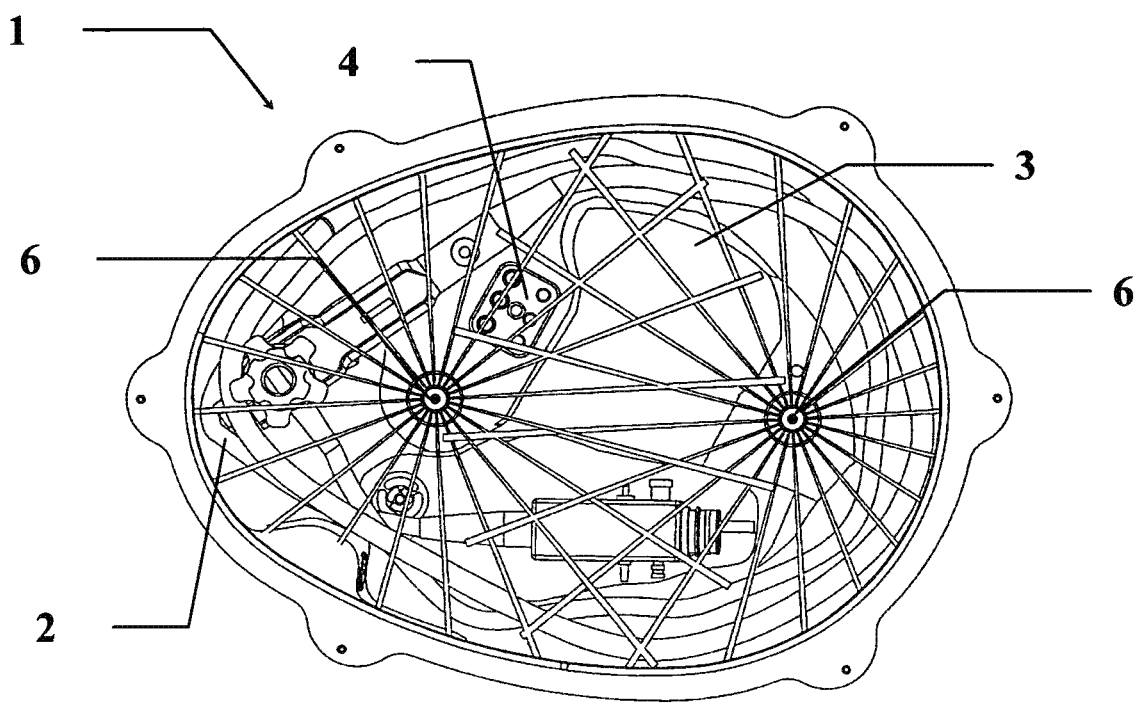
FIG. 1 represents an open top view of a treatment machine with a medical apparatus in position.

The invention relates to a treatment machine for a medical apparatus comprising inner portions and outer portions, such as a flexible endoscope, whereas said machine contains a hollow vessel capable of receiving said medical apparatus, a first treatment system capable of treating the inner portions of the medical apparatus and a second treatment system capable of treating the outer portions of the medical apparatus, characterised in that: said first treatment system comprises a means for connecting at least one end piece of the medical apparatus so as to enable treatment liquid to circulate in its inner portion, preferably a means for connecting the different end pieces of the medical apparatus so as to establish the circulation of treatment liquid in a leak-proof manner and in that said second treatment system comprises:
at least one spray nozzle capable of receiving at least one pressurised treatment liquid and of projecting vigorously said treatment liquid into the volume of the vessel, so as to perform a treatment of the outer portions of the medical apparatus and of the inner surfaces of the vessel by spraying while creating a mechanical effect and a chemical effect,
still at least one means for filling the vessel capable of filling, at least partially, said vessel with at least one treatment liquid, so as to perform a treatment of the outer portions of the medical apparatus and the inner surfaces of the vessel by immersing, at least partially.

According to another characteristic of the invention, the vessel is substantially elliptical in shape and the second treatment system comprises two spray nozzles more or less arranged in the focal points.

According to another characteristic of the invention, the spray nozzle comprises a base for fastening the spray nozzle to the bottom of the vessel and for fluidic connection of the spray nozzle to a device for dispensing the pressurised treatment liquid and a diffuser for projecting said treatment liquid.

According to another characteristic of the invention, the base comprises a removable fastening means to the bottom of the vessel. Advantageously according to the invention, the base is substantially conical, is not integral with the vessel and comprises a removable fastening means to the bottom of the vessel.

According to another characteristic of the invention, the diffuser is substantially cylindrical, the cylindrical surface is drilled with a plurality of holes linking an axial duct connected to said device for dispensing the pressurised treatment liquid outside the spray nozzle.

According to another characteristic of the invention, the holes are distributed regularly over the cylindrical surface.

According to another characteristic of the invention, the axes of the holes are radial and perpendicular to the axis of the diffuser.

According to another characteristic of the invention, the diffuser is immovable relative to the base, so that the holes remain immovable relative to the vessel during the operation of the treatment machine.

According to another characteristic of the invention, the distal end of the diffuser is drilled with an orifice connecting said axial duct outside the spray nozzle.

The invention still relates to a method for treating a medical apparatus comprising inner portions and outer portions, such as a flexible endoscope, by means of a machine according to the invention, including the following steps:

spraying the outer portions of the medical apparatus and the inner surfaces of the vessel with at least one treatment liquid by means of at least one spray nozzle,
immersing, at least partially, the outer portions of the medical apparatus and the inner surfaces of the vessel into at least one treatment liquid by filling, at least partially, the vessel by means of said filling means, whereas said immersing step is performed prior, concomitantly or posterior to the spray step, treating the inner portions of the medical apparatus by means of the first treatment system comprising a means for connecting at least one end piece of the medical apparatus so as to enable treatment liquid to circulate in its inner portion, preferably a means for connecting the different end pieces of the medical apparatus so as to establish a circulation of treatment liquid in a leak-proof manner, whereas said treatment step is performed prior, concomitantly or posterior to the spray and/or immersing steps.

According to another characteristic of the invention, the spray step re-uses the treatment product.

According to another characteristic of the invention, the spray step, respectively the immersing step, re-uses the treatment product used by the immersing step, respectively the spray step.

According to an alternative feature of the invention, the spray step, respectively the immersing step, uses clean treatment product.

Figure 2:
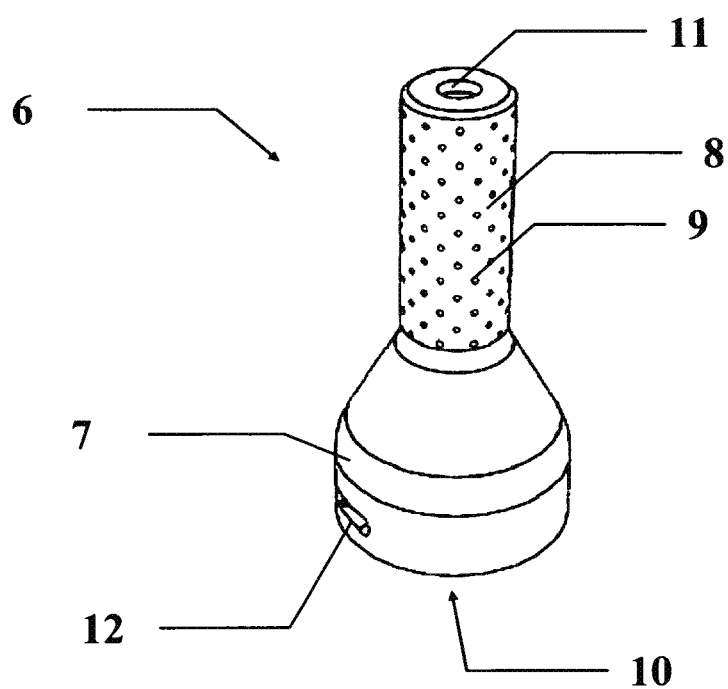
FIG. 2 represents a perspective view of a spray nozzle according to an embodiment.

Other characteristics, details and advantages of the invention will become readily apparent by reference to the detailed description given below for information purposes in relation to drawings in which:

FIG. 1 represents an open top view of a treatment machine with a medical apparatus in position, FIG. 2 represents a perspective view of a spray nozzle according to an embodiment.

According to FIG. 1, a treatment machine 1 can be seen from above, with the vessel 3 open. A medical apparatus 2 is in position in the vessel, ready for a cleaning/disinfection cycle. According to the invention, the treatment machine 1 is particularly suited to the treatment of the outer portions of said medical apparatus 2. It also enables at the same time to treat inner portions of said medical apparatus 2 and is thereby particularly suitable for the treatment of a medical apparatus 2 comprising inner and outer portions to be treated. An endoscope for example is a flexible medical apparatus, which may have quite variable conformations, but is characterised by one or several connected flexible tubular channels and which should be treated internally as well as externally.

A treatment machine 1 must meet the regulatory constraints as specified in the standards ISO 15883-1 and ISO 15883-4. Thus, a treatment of a medical apparatus must comprise several successive cycles, i.e. cleaning, rinsing and disinfection in a set order, while contacting inner as well as outer portions of the medical apparatus 2 with various chemicals.

To do so, such a treatment machine 1 contains a hollow vessel 3 capable of receiving said medical apparatus 2. Said vessel may for instance comprise a lid which can be opened for placing the medical apparatus 2 before treatment and removing it after treatment. Said lid can still be closed in a liquid-proof manner during the operation of the treatment machine.

If needed, if the medical apparatus 2 comprises inner portions to be treated, the treatment machine 1 may advantageously comprise a first treatment system 4 capable of treating the inner portions of the medical apparatus 2.

As the volume of the inner portions is reduced most often, it is advantageously treated by internal circulation of the chemicals. The first treatment system 4 is similar to the prior art and is consequently not described in detail here. It comprises a means for connecting at least one end piece of the medical apparatus so as to enable treatment liquid to circulate in its inner portion, preferably a means for connecting the different end pieces of the medical apparatus 2 so as to establish the circulation of treatment liquid in a leak-proof manner.

The treatment machine 1 still comprises a second treatment system capable of treating the outer portions of the medical apparatus 2.

According to the previous art, the outer portions are treated by immersing, which means that the vessel 3 is filled with the chemicals used successively during the treatment. Given the necessary volume of the vessel 3 to accommodate the medical apparatus 2, which is quite significant with respect to the volume effectively occupied by said medical apparatus 2, such an embodiment leads to a large and detrimental consumption of chemicals.

To remedy this major shortcoming, according to the invention, the second treatment system functions following a spray principle. Immersing the medical apparatus 2 into a large volume of chemical is mainly replaced with spraying using the same chemical, and the amount of chemical is vastly reduced.

Moreover, spraying enables to add to the chemical effect of the treatment product a mechanical effect which improves the treatment and thus enables to further reduce the necessary amount of chemical.

To perform this spraying operation, the second treatment system includes at least one spray nozzle 6 capable of receiving at least one pressurised treatment liquid/chemical and of projecting vigorously said treatment liquid into the volume of the vessel 3.

Spraying thus made enables to treat the outer portions of the medical apparatus 2. Moreover, it still enables to treat the inner surfaces of the vessel 3.

Spraying may be carried out using throughout a spraying phase the same clean treatment product permanently. This ensures the best possible quality of treatment.

Alternately, to improve the savings on treatment product still further, it is possible to recycle this treatment product during said phase. Thus, the treatment product can be recovered, for example at the bottom of the vessel 3 where it trickles after being sprayed, to be re-used, via said at least one spray nozzle 6 for being sprayed again during the same phase.

According to an advantageous embodiment, immersing, at least partially, can be employed in complement to spraying. Said advantageously partial immersing enables to improve the treatment of the lower section of the vessel 3, hardly achievable directly by spraying by means of said at least one spray nozzle 6.

Advantageously, for optimal operation of the spray nozzle 6 and limited usage of chemicals, by immersing is meant immersing the medical apparatus 2 into an amount of chemicals up to the base 7 of the spray nozzle 7.

Advantageously, immersing is carried out using at least one filling means comprising for instance at least one orifice placed at the bottom of the vessel 3. Other orifices, or the same orifices, may then serve for draining the vessel 3. According to an embodiment, the filling means may then be said at least one spray nozzle 6. The sprayed treatment liquid, flowing after spraying towards the bottom of the vessel 3 and causing at least partial immersing the medical apparatus 2 and the vessel 3.

When both spraying and immersing steps are used, immersing may take place before, during or after spraying. The two steps sharing the same vessel 3 must be conducted with the same type of treatment liquid, if they temporally overlap each other at least partially.

As regards the treatment of the inner portions of the medical apparatus 2, it is completely independent. It may consequently be performed before, during or after the spraying and/or immersing steps. Advantageously, treating the inner portions of the medical apparatus 2 is made in a leak-proof manner. Impermeability still enables to use concomitantly types of treatment liquid which are on the one hand different for the inner portions and on the other for the outer portions of the medical apparatus 2. Alternately, to improve the savings on treatment product, treating the inner portions of the medical apparatus 2 is not conducted in a leakproof manner, whereas the treatment product used then flows to the bottom of the vessel 3. Said treatment product used may then be collected and re-used, for example via said at least one spray nozzle 6 for spraying.

To obtain the best possible quality of treatment, spraying and immersing are advantageously performed with clean treatment product.

Alternately, to improve the savings on treatment product, spraying may re-use the treatment product used by immersing, before or during spraying. Similarly, it may be envisioned to re-use for immersing, the treatment product used, before or during, by spraying.

Numerous configurations of treatment machine have been studied, comprising different shapes of vessel and one or several spray nozzles 6 arranged in different locations.

A particularly efficient configuration in terms of treatment with respect to the consumption of chemical proved to be a vessel substantially elliptical in shape, whereas the second treatment system comprises two spray nozzles 6 more or less arranged in the focal points of said ellipse. Such an arrangement enables the spray nozzles 6 to produce efficient spraying of the chemicals throughout the vessel 3, while maintaining a reduced distance between a spray nozzle 6 and the medical apparatus 2, to guarantee the mechanical cleaning effect. Such an arrangement enables placing the medical apparatus 2 forming an O or an 8 around both spray nozzles 6.

As illustrated on FIG. 2, a spray nozzle 6, according to an embodiment, comprises a base 7 for fastening the spray nozzle 6 to the bottom of the vessel 3. Said nozzle 7 still enables fluidic connection of the spray nozzle 6 to a device for dispensing a pressurised treatment liquid. The treatment liquid thus received by the base 7 from the spray nozzle 6 runs through a substantially cylindrical central duct 10 arranged along the axis of the spray nozzle 6. It enables to supply said cleaning liquid to a diffuse 8 in the extension of said base 7. The diffuser 8 enables the projection of said treatment liquid throughout the volume of the vessel 3 and over the outer portions of the medical apparatus 2.

According to an embodiment, the base 7 comprises a removable fastening means 12 enabling the fixed mounting thereof to the bottom of the vessel 3. Thus the base 7, as well as the spray nozzle 6 in its entirety, are held immobile, during the cleaning operation of the treatment machine 1. The same fastening means 12 enables disassembly of the spray nozzle 6, so as to clean it or, if required, to replace it. This fastening means 12 comprises, for instance, a screw- or still bayonet-type, advantageously a quarter turn-type device, to guarantee reliable fastening as well as quick assembly and disassembly without using tools.

According to an embodiment, the diffuser 8 is a substantially cylindrical and extends over a large portion of the height of the vessel 3. The cylindrical surface is advantageously drilled with a plurality of holes 9. Each of said holes 9 links the central axial duct 10 made in the spray nozzle 6 outside the spray nozzle 6. Said central duct 10 is connected to a device for dispensing pressurised treatment liquid through which said treatment liquid arrives. The suited pressure of treatment liquid, combined with the holes 9 enables to create a projection of said treatment liquid in all the directions concerned by said holes 9. The arrangement of the holes 9; distributed evenly over the whole height of the diffuser 8, as well as angularly distributed evenly over the whole periphery of the diffuser 8, or still along an even spatial distribution over the whole cylindrical surface of the diffuser 8, enables omnidirectional diffusion of the chemical throughout the volume of the vessel 3.

In a preferred embodiment, the axes of the holes 9 are radial and perpendicular to the axis of the diffuser 8.

Planar apertures made in the diffuser 8 provide according to an alternative embodiment a comparable radially omnidirectional diffusion, but make the diffuser 8 too brittle.

Conversely, an arrangement of the holes 9 in quincunx enables regular arrangement while preserving the structural solidity.

An adapted pressure of treatment liquid, according to the cumulative total surface area of the holes 9 and orifices 11, enables to obtain jets of treatment liquid which are strong enough to produce a suitable effect of mechanical cleaning. Said pressure may advantageously be determined empirically.

Another embodiment for obtaining radially omnidirectional diffusion is a use of a spray nozzle 6/of a rotary diffuser 8. Such a rotation can be produced by a motorised system or by the effect of the circulation of the pressurised treatment liquid. However within the secured context of the treatment of a medical apparatus 2, one such approach has the serious shortcoming in that it may cause a failure by stopping/blocking the rotation, which is difficult to detect, and the result may be a non- or poorly treated medical apparatus 2 even though it may have been subjected to a supposedly complete, seemingly complying and certified treatment. To do so according to the invention, a diffuser 8, immovable relative to the vessel 3 and thus immovable relative to the medical apparatus 2, during the operation of the treatment machine 1, is advantageous preferred. This realised by a spray nozzle 6 where the diffuser 8 is immovable relative to the base 7, whereas the base 7 is immovable relative to the vessel 3, so that the holes 9 remain immovable relative to the vessel 3. The omnidirectional spraying is then obtained by a plurality of regularly distributed holes.

According to an embodiment, the holes 9 have a diameter of 1 mm.

According to an illustrative embodiment, the holes 9 are 140 in number, spread regularly on a surface of cylindrical diffuser 8 of outer diameter smaller than 18 or of height 45 mm. Which means a hole density of 140 holes for a surface area of approx. 25.5 $cm^2$, i.e. more or less 5.5 holes/$cm^2$.

According to an advantageous embodiment, the distal end of the diffuser 8 is drilled with an orifice 11. Said orifice 11 links the axial duct 10 outside the diffuser 8 of the spray nozzle 6. This enables to spray the ceiling of the vessel 3. This provides efficient treatment of said ceiling and completes the spraying performed by the holes 9.

The spray nozzle 6 must sustain the corrosion and the chemical aggressions of the chemicals used as treatment liquids. Moreover, it must hold the high pressure which may be used for the treatment liquid. For cleaning purposes, the disassembled spray nozzle 6 may advantageously be cleaned/disinfected in a high temperature stove. To withstand all these constraints, the spray nozzle 6 is advantageously made of stainless steel, for example of 316 L-type.

We claim:

1. A method comprising:
   positioning an endoscope in a vessel having a sidewall and a bottom wall that collectively define a hollow cavity, the vessel comprising two spray nozzles projecting upwardly from the bottom wall of the vessel into the hollow cavity, wherein positioning the endoscope comprises wrapping the endoscope around the two spray nozzles, including positioning the endoscope in at least two of a first medical device receiving space between the sidewall and a first one of the two spray nozzles, a second medical device receiving space between the sidewall and a second one of the two spray nozzles, and a third medical device receiving space between the first and second spray nozzles;
   at least partially filling the vessel with a treatment liquid to at least partially immerse an outer portion of the endoscope in the treatment liquid in the vessel;
   spraying the outer portion of the endoscope with the treatment liquid through each of the two nozzles, wherein spraying the outer portion of the endoscope comprises spraying the treatment liquid radially through each of the two nozzles against the outer portion of the endoscope; and
   passing the treatment liquid through an interior of the endoscope.

2. The method of claim 1, wherein positioning the endoscope in at least two of the first medical device receiving space, the second medical device receiving space, and the third medical device receiving space comprises positioning a first portion of the endoscope in the first medical device receiving space, positioning a second portion of the endoscope in the second medical device receiving space, and positioning a third portion of the endoscope in the third medical device receiving space.

3. The method of claim 1, wherein spraying the outer portion of the endoscope with the treatment liquid comprises spraying the outer portion of the endoscope with the treatment liquid in which the endoscope was at least partially immersed.

4. The method of claim 1, wherein spraying the outer portion of the endoscope with the treatment liquid comprises spraying the outer portion of the endoscope prior to or concomitantly with at least partially filling the vessel with the treatment liquid.

5. The method of claim of claim 1, wherein the two spray nozzles each comprise a base fastened to the bottom wall of the vessel, and at least partially filling the vessel with the treatment liquid comprises filling the vessel with the treatment liquid up to the base of each spray nozzle.

6. The method of claim 1, wherein positioning the endoscope in the vessel comprises forming the endoscope into an O-shape passing through the first medical device receiving space and the second medical device receiving space.

7. The method of claim 1, wherein positioning the endoscope in the vessel comprises forming the endoscope into an 8-shape passing through the first medical device receiving space, the second medical device receiving space, and the third medical device receiving space.

8. The method of claim 1, wherein the vessel defines an elliptical shape.

9. The method of claim 8, wherein:
   the elliptical shape defines two focal points,
   the first one of the two spray nozzles is located at a first of the two focal points, and
   the second one of the two spray nozzles is located at a second of the two focal points.

10. The method of claim 1, wherein passing the treatment liquid through the interior of the endoscope comprises connecting at least one tubular channel end piece of the endoscope to a treatment system and circulating the treatment liquid through the at least one tubular channel end piece.

11. The method of claim 1, wherein spraying the outer portion of the endoscope with the treatment liquid through each of the two nozzles comprises spraying the treatment liquid through each of the two nozzles omnidirectionally through a volume of the vessel.

* * * * *

UNITED STATES PATENT AND TRADEMARK OFFICE
CERTIFICATE OF CORRECTION

Page 1 of 1

PATENT NO. : 10,874,478 B2
APPLICATION NO. : 16/584407
DATED : December 29, 2020
INVENTOR(S) : Tanguy Dromard, Eric Pendaries and Sebastien Ruiz It is certified that error appears in the above-identified patent and that said Letters Patent is hereby corrected as shown below:

In the Claims

In Column 8, Claim 5, Line 29, delete "of claim of claim" and insert -- of claim --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*